United States Patent
Kurtz

(10) Patent No.: US 9,414,847 B2
(45) Date of Patent: Aug. 16, 2016

(54) PATIENT SPECIFIC SOFT TISSUE PROTECTORS AND RETRACTORS

(71) Applicant: William B. Kurtz, Nashville, TN (US)

(72) Inventor: William B. Kurtz, Nashville, TN (US)

(*) Notice: Subject to any disclaimer, the term of this patent is extended or adjusted under 35 U.S.C. 154(b) by 236 days.

(21) Appl. No.: 14/059,372

(22) Filed: Oct. 21, 2013

(65) Prior Publication Data

US 2014/0114320 A1     Apr. 24, 2014

Related U.S. Application Data

(60) Provisional application No. 61/716,571, filed on Oct. 21, 2012.

(51) Int. Cl.
    *A61B 17/15*     (2006.01)
    *A61B 17/56*     (2006.01)

(52) U.S. Cl.
    CPC .............. *A61B 17/157* (2013.01); *A61B 17/155* (2013.01); *A61B 2017/568* (2013.01)

(58) Field of Classification Search
    CPC ............... A61B 17/155; A61B 17/157; A61B 2017/568
    See application file for complete search history.

(56) References Cited

U.S. PATENT DOCUMENTS

2011/0245835 A1*   10/2011   Dodds .................. A61B 17/155
                                                          606/87

* cited by examiner

*Primary Examiner* — David Bates
*Assistant Examiner* — Olivia C Chang
(74) *Attorney, Agent, or Firm* — Brainspark Associates, LLC

(57) ABSTRACT

Disclosed are devices, methods and/or systems for tissue protectors and/or retractors having patient specific and/or patient adapted features that facilitate the accuracy and predictability of bone resection and tissue preparation during joint surgery, as well as improve the distraction of soft tissues, desirably preventing accidental injury to surrounding soft tissue structures and improving visualization.

20 Claims, 12 Drawing Sheets

PATIENT SPECIFIC SOFT TISSUE PROTECTORS AND RETRACTORS

CROSS-REFERENCE TO RELATED APPLICATIONS

This application claims the benefit of U.S. Provisional Patent Application Ser. No. 61/716,571 entitled "Patient Specific Soft Tissue Protectors," filed Oct. 21, 2012, the disclosure of which is incorporated by reference herein in its entirety.

TECHNICAL FIELD

The invention relates to improved orthopedic tools and methods for use during orthopedic surgical procedures, including joint replacement procedures. More specifically, disclosed herein are improved methods, apparatus and/or systems for soft tissue protector and/or retractors that facilitate accuracy and predictability of bone resection during joint surgery, and desirably prevent accidental injury to surrounding soft tissue structures.

BACKGROUND OF THE INVENTION

Patient specific and standard sized bone resection cutting guides ("cutting guides") are well known in joint replacement surgery. Cutting guides help the surgeon prepare the patient's anatomical structures (i.e., bone) for ideal positioning of joint replacement components, such as knee implant components, for optimal joint balancing and prosthesis positioning. Bone resection accuracy is important as the resected bone surfaces can influence the positioning and/or orientation of implant components, which have a resulting effect on implant performance, patient mobility/stability and prosthesis long-term efficacy. Many cutting guides have a variety of cutting guide structures and/or surfaces, such as flat surfaces, slotted cutting surfaces or adjustable slotted surfaces. Typically, a surgeon will make an incision into and through the skin and soft tissues to access a patient's bony structures. In many instances, soft tissue structures will be released or otherwise modified, especially where they obstruct the selected bone surface for resection. In most cases, however, there are at least some surrounding soft tissue structures that are maintained intact to provide stability for the treated extremity and facilitate patient rehabilitation of the treated structures to desirably restore native function and movement in the joint.

Since many surrounding soft tissue structures are desirably unaffected and/or unmodified during a given joint surgery procedure, a surgeon cutting into and/or through bone and/or soft tissue structures must be careful to follow the various cutting guide surfaces with their saw blade or other cutting or drilling tool. Surrounding soft tissue structures will desirably be avoided, as unintentional damage to such areas can cause significant tissue damage and/or significantly degrade the outcomes resulting from the surgical procedure. Moreover, cutting depth control can also be important during a surgical procedure, as the cutting tools can unintentionally exit the intended bone or other cut tissues, with potentially negative consequences for surrounding tissues.

In many cases, it can be difficult to predict whether a given surgical cut will accidentally cut something other than an intended bone or other tissue structure, especially where the entire periphery of the structure being cut cannot be directly and/or indirectly visualized. There can be multiple contributing factors that result in unintentional injury or damage (i.e., cutting) of surrounding tissue structures, such as improper positioning and/or movement of the cutting guide, saw blade deflection, saw blade toggle, movement of the saw blade within the clearance slots of the guide, and/or over-extension (i.e., excessive advancement) of the saw blade, drill or rongeur (or other cutting devices) into surrounding soft and/or hard tissue structures. As previously noted, an accidental injury to surrounding tissues can have significant consequences for the patient, including excessive bleeding, tissue or nerve damage and infection, as well as possibly delaying the patient's recovery and/or creating joint instability that leads to an inability to restore or rehabilitate the patient's native and/or desired joint kinematics.

Traditionally, surgeons have attempted to protect surrounding hard or soft tissue structures by placing rigid retractors or other devices between the edges of the bone (where they anticipate the saw blade might exit the bone) and the protected tissues, desirably to protect these tissue structures from accidental injury from cutting tools. Such retractors are typically designed with various standard arches, curvatures, shapes, sizes and/or widths, and a number of such sizes and shapes are often provided in a kit. But there is no guarantee that these "standard" shapes and sizes will be an appropriate fit for a selected anatomical structure of the joint, creating an uncertainty that a selected retractor will be in an appropriate position to protect adjacent hard or soft tissue structures from an accidental excursion of the saw blade. Moreover, numerous separate attachments, tools or fixtures might be necessary to maintain a given retractor's position during resection of the bone. In addition, where a surgical retractor is manually held in a desired position (i.e., by a handle), the retractor may slide off the bone and/or move unintentionally during the cutting procedure or may not have been positioned in a correct location in the first place, thus increasing the chances of cutting or injuring surrounding hard or soft tissue structures.

BRIEF SUMMARY OF THE INVENTION

The invention disclosed herein includes the realization of a need for an improved tissue retractor or "cutting shield" design ("soft tissue protector") that desirably inhibits and/or prevents accidental injury or cutting of surrounding hard and/or soft tissues while its intended position can be easily and accurately maintained during bone or other tissue resection. The soft tissue protector may be useful in any contemplated joint surgery, including, but not limited to, shoulder, wrist, ankle, hip, knee, spine (i.e., interbody vertebral fusion, anterior cervical discectomy and fusion, wedge osteotomy, and/or facets, costoverterbral joints, contravertebral joints, etc.), elbow, and any facial reconstruction.

In various exemplary embodiments, the soft tissue protector may include patient-specific features and/or contours, which can be created using various two-dimensional (2D) and/or three-dimensional (3D) images of the patient's anatomy taken preoperatively. Such images can be taken statically and/or dynamically, which could include during studies of a patient's pre-operative range of motion, pre-operative flexion contracture, pre-operative extension lag, pre-operative ligament balancing, pre-operative ligament tension, and/or pre-operative coronal alignment. Using the provided images, a designer can derive a set of specific dimensions and/or surface contours for relevant patient anatomy to design one or more soft tissue protectors for use in protecting important tissue structures, and such tissue protectors could be utilized in conjunction with various surgical cutting guides available on the market and/or with specific manufacturer's surgical cutting guides.

In various exemplary embodiments, a soft tissue protector may be designed as single independent components or the protector may be integrated into and/or function in conjunction with one or more surgical cutting guide (i.e., femoral and/or tibial cutting guides). A manufacturer may design tissue protectors in a variety of ways. For example, one embodiment of a tissue protector may include patient-specific contours that exactly match various anatomical features of a targeted region of the patient's body. Another embodiment may include contours that approximate or partially-match various anatomical features of a targeted region of the patient's body. Other embodiments might include protectors incorporating one or more contours derived from a database library of historical patient data images, with a plurality of protectors provided in a kit that could be individually used or could be used in conjunction with various cutting guides, such as one or more types of tibial and/or femoral cutting guides. In various embodiments, the protectors can be designed to integrate and/or work in conjunction with a single design or type of cutting guides, or can be designed to integrate and/or work in conjunction with a plurality of different manufacturer's designs. Where a protector attaches to or otherwise integrates with a cutting guide, the resulting tool might be usable as a complete unit, allowing one-handed positioning, adjustment and/or operation by a surgeon, if desired.

In various exemplary embodiments, a protector may include one-sided and/or two-sided contouring. "One-sided contouring" may comprise a protector having a single side that is contoured to match or substantially conform to a desired section of the patient's anatomy. In contrast, "two-sided contouring" may comprise a protector having two or more "sides" (which could include generally opposing sides of the device, as well as features on differing ends of the device), each of which are contoured to match or substantially conform to a different portion of the patient's anatomy. "Two-sided contouring" could include a protector designed to fit between opposing joint surfaces of a patient's joint, such as between the tibia and femur of a knee joint.

In various exemplary embodiments, a protector may include features that protect a plurality of sides of a patient's anatomy "One-sided" protection may be intended to align with a single surface (including complex curvatures) and/or bone feature, shielding the surrounding anatomy from a single side of the bone surface during resection. For example, during total knee replacement, a manufacturer might design individual soft tissue protectors to protect both the medial side and the lateral side of the knee, thus desirably preventing injury to the MCL and the LCL. Alternatively, a "multi-sided" protector design might include features that surround a periphery of the bone, desirably to protect at least two sides of a bone. For example, during total knee replacement, the manufacturer may design a single soft tissue protector to sit adjacent to and protect the medial, posterior and lateral side of the bone.

DETAILED DESCRIPTION OF THE INVENTION

The disclosures of the various embodiments described herein are provided with sufficient specificity to meet statutory requirements, but these descriptions are not necessarily intended to limit the scope of the claims. The claimed subject matter may be embodied in a wide variety of other ways, may include different steps or elements, and may be used in conjunction with other technologies, including past, present and/ or future developments. The descriptions provided herein should not be interpreted as implying any particular order or arrangement among or between various steps or elements except when the order of individual steps or arrangement of elements is explicitly described.

Various embodiments described herein include the design and manufacturing of patient specific and/or patient adapted retractors and/or tissue protectors having various pre-defined shapes, sizes, widths, spans, thicknesses and/or contours based, at least partially, off of anatomical shape information obtained from one or more pre-operative scans (i.e., x-ray, sonogram, CT scan, MRI, etc.) of the patient's anatomy. Various embodiments described herein can be used as individual surgical tools to protecting adjacent tissue structures from cutting tools (including, but not limited to, physical cutting tools as well as electrical and/or optic/laser ablative cutting tools), while other embodiments include features that allow attachment to, engagement with and/or alignment against surgical cutting guides, including patient specific cutting guides. Desirably, portions of the tissue protector will lie between adjacent tissues and hard and/or soft tissue requiring resection and/or other surgical modification.

Various embodiments described herein can be used in conjunction with patient specific cutting guides that have been constructed specifically for an individual patient, including guides where the contour of the guide is a reverse mold of the patient's bony surface. The shape of such guides can be determined from scans or digital images like a CT Scan or a MRI. In many cases, such cutting guides can help the surgeon determine an ideal position for cutting and/or preparing anatomical structures for receiving implant components, such as knee replacement components.

Figure 1A:
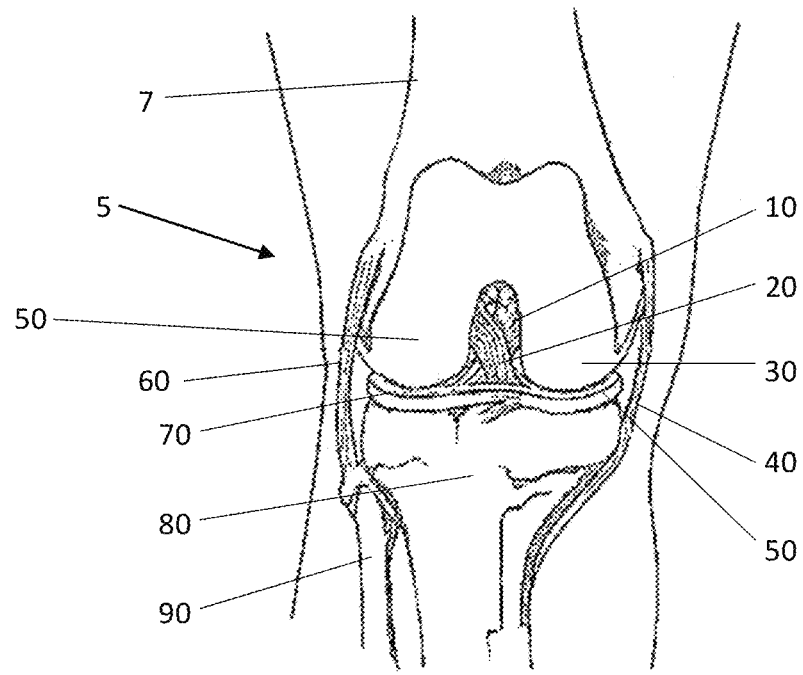
FIG. 1A depicts a perspective view of a knee joint, showing associated hard tissue structures and soft connective tissues.

FIG. 1A shows a perspective view of a knee joint 5, with associated hard tissue structures and soft connective tissues between the major bones, and the patella removed. The knee joint includes a femur showing a tibia 80, a fibula 90 and a femur 7, the femur comprising a medial condyle 30 and a lateral condyle 50. A number of connective tissues extend between the various bony structures of the knee, including the medial collateral ligament 40 (MCL), the lateral collateral ligament 60 (LCL), the posterior cruciate ligament 20 (PCL) and the anterior cruciate ligament 10 (ACL). Also shown are the medial 50 and lateral 70 portions of the meniscus.

Figure 1B:
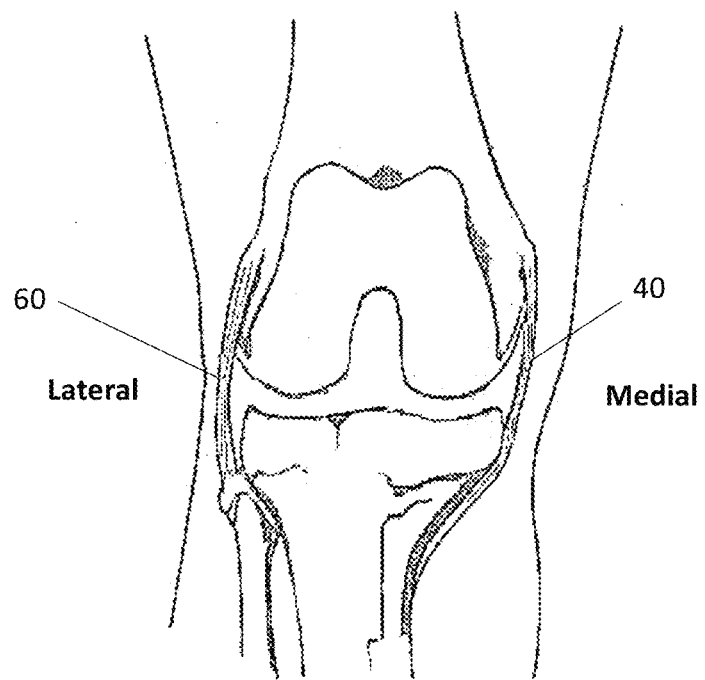
FIG. 1B depicts a frontal view of the knee joint of FIG. 1; with various tissue structures removed.
Figure 2:
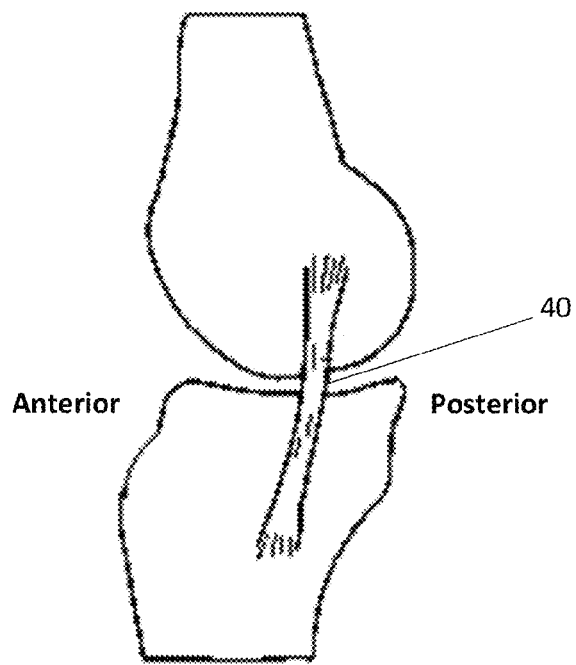
FIG. 2 depicts a side view of the knee joint of FIG. 1B.

FIG. 1B shows the knee joint of FIG. 1, with various soft tissues removed. In many total knee replacement procedures, some of the softer tissues normally found between the femur and the tibia will be surgically removed, as well as various portions of the femoral and tibial bone surfaces that are prepared and/or removed to accommodate femoral and tibial implant components. However, a surgeon performing a total knee replacement will typically seek to retain both the medial and lateral collateral ligaments 40 and 60, as the integrity of these structures will be critically important to the proper stability and performance of the knee joint and the treated lower extremity. FIG. 2 shows is a side view of the knee joint of FIG. 1B, including exemplary bony attachment points of the medial collateral ligament 40.

In various embodiments, retractors and/or tissue protectors such as those described herein can be used in conjunction with cutting guides that are standard, modular and/or non-patient adapted. If desired, the various features of the retractors and/or protectors described herein, including any patient-specific features, could be utilized to align and/or otherwise position a standard or modular cutting guides in a desired location, orientation and/or other manner, which could include effectively converting a standard cutting guide into a patient-specific cutting guide.

Figure 3:
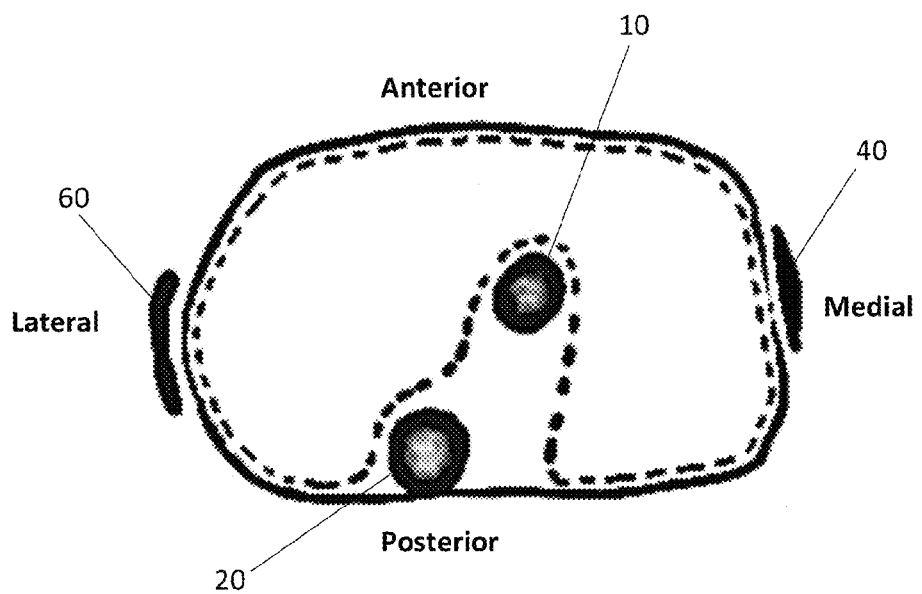
FIG. 3 depicts a top view of a tibia illustrating a common location of an ACL and PCL.

When a surgeon is using a cutting guide (including either or both of patient specific or generic guides), the surgeon will desirably carefully observe the excursion of the oscillating saw blade (if possible) so that the saw blade does not accidental cut something other than the intended bone. For example, when preparing a tibial bone for accepting a tibial tray implant, the entire horizontal cut through the tibia should be carefully monitored to minimize contact with other surrounding tissues. If not properly controlled, a saw blade can at times extend through an intended bone cut and injure a soft tissue structure on an opposing side of the bone, or the blade can extend horizontally beyond the bone that is being cut. An accidental injury to the surrounding soft tissue structures might include damage to important structures in the vicinity of the cut, which in a knee joint could include (but is not limited to) the medial collateral ligament (MCL) 40, the lateral collateral ligament (LCL) 60, various posterior neurovascular structures (popliteal artery/vein & posterior tibial nerve), the patellar tendon and/or the skin. In addition, various saw cuts or other surgical dissections could cause unintended damage to the anterior cruciate ligament 10 or the posterior cruciate ligament 20 (see FIG. 3), where the retention of such tissue structures was desired. If one or more of these various structures was accidental cut or injured in some manner, the patient might suffer grave consequences, which could include instability of the resulting joint implant and/or complete failure of the surgical repair.

To reduce the opportunity for unintentional injury to surrounding tissue structures, surgeons will often place special metal retractors (i.e., Zknee™ retractors) around the edges of a bone where the surgeon may anticipate a saw blade could exit from the bone (during a given cutting procedure), desirably protecting various soft tissue structures from accidental injury. However, because patient anatomical structures widely vary among human populations, and because such retractors are often advanced "blindly" into a wound (i.e., the retractor and adjacent tissues are typically not be easily visualized by the surgeon), there is no certainty that the retractor will be in an appropriate position and/or orientation to protect the soft tissue structures from an accidental excursion of the saw blade. If the retractor is improperly placed and/or oriented, if a surgical assistant moves a retractor during the surgical procedure, or if the saw blade or other surgical tools displace the retractor during the cutting procedure, the soft tissue structures might still be injured, despite the use of such standard retractors.

Figure 4A:
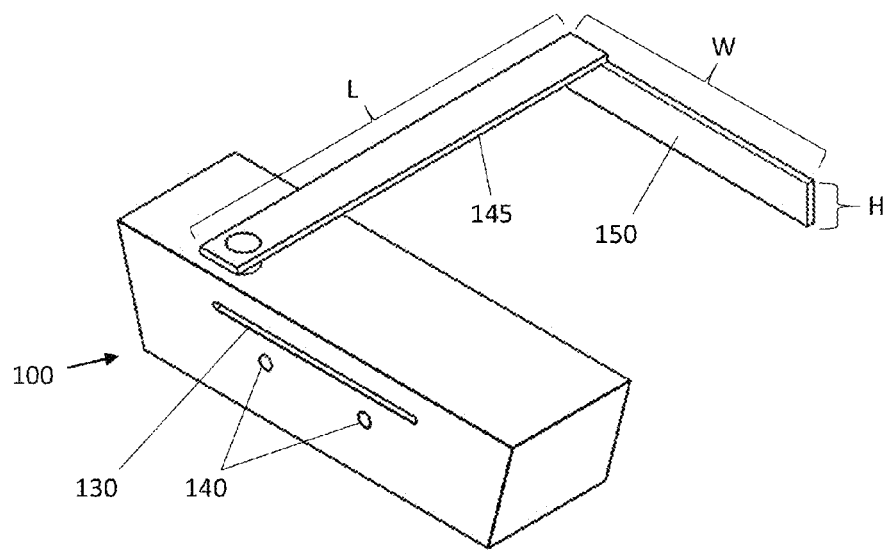
FIG. 4A depicts a perspective view of a cutting guide and one embodiment of an integrated tissue protector.

To address various shortcomings of existing retractors and associated cutting guides, various embodiments described herein contemplate the design and manufacturing of patient-specific and/or patient-adapted tissue protectors for use in surgical procedures. FIG. 4A depicts a perspective view of a cutting guide and one embodiment of a tissue protector including patient-specific features. In this embodiment, one or more of the length (L), width (W) and/or height (H) of the tissue protector can be preoperatively determined based upon one or more pre-operative scans (i.e., x-ray, sonogram, CT scan, MRI, etc.) of the patient's anatomy. Where the various dimensions and/or features of the cutting guide and patient's anatomy are known, an appropriate tissue protector for use with the patient's anatomy can be designed and manufactured prior to the surgical procedure.

Figure 4B:
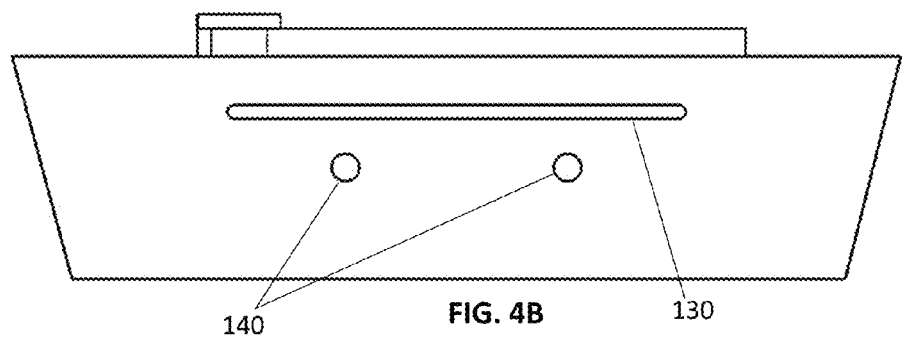
FIG. 4B is a front plan view of the guide and protector of FIG. 4A.
Figure 4C:
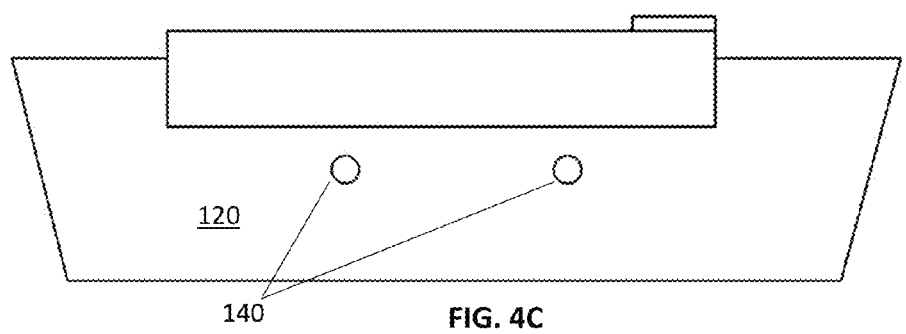
FIG. 4C is a rear plan view of the guide and protector of FIG. 4A.

A surgical cutting guide, such as the one depicted in FIGS. 4A through 4C, can be a standard or modular cutting guide, or can include various patient-specific features, if desired. The cutting guide 100 can include a guide body 110 having a bone-facing surface 120, a guiding surface or slot 130 and one or more pin openings 140. Attached to the cutting guide body 110 is a tissue protector having a blocking surface 150 and an extension arm 145. Desirably, the dimension and/or shape of the extension arm can be designed and/or selected, using the anatomical image data, to match the thickness of a bone or other anatomical structure, which in the disclosed embodiment could be the anterior/posterior width of the tibial plateau (not shown). The blocking surface 150 can be selected such that it extends downwards into the cutting plane defined by the slot 130, thereby inhibiting passage of a saw blade or other cutting tool. The width of the blocking surface can similarly be designed to reflect the extent of various patient-specific anatomy to be protected (i.e., which may reflect the location of the various anatomical structures to be protected) and/or can be sized or otherwise designed to reflect the maximum extent the surgical tool can extend within the slot 130, if desired. In this embodiment, the extension arm 145 can be detachably or permanently connected to the cutting guide body 110, and the extension arm can desirably be designed using patient-specific anatomical information to avoid intervening anatomical features on the tibia, if desired.

Figure 5A:
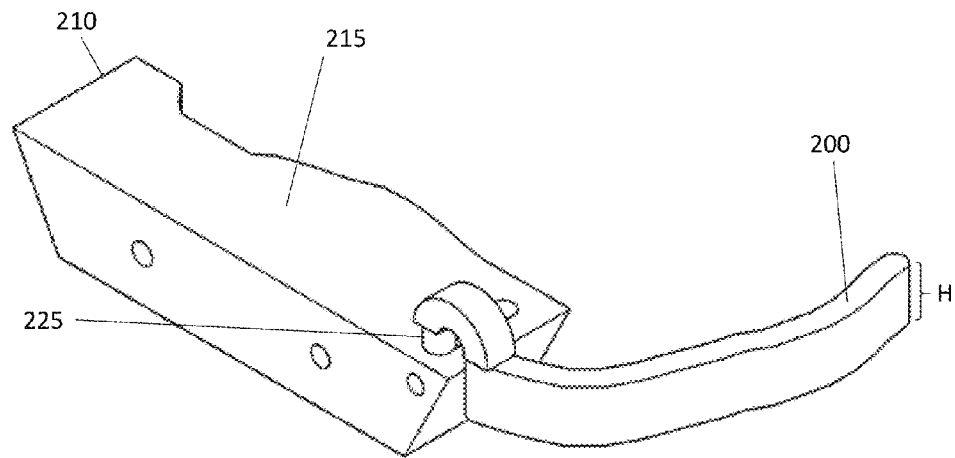
FIG. 5A depicts a perspective view of a cutting guide and another exemplary embodiment of an integrated tissue protector.
Figure 5B:
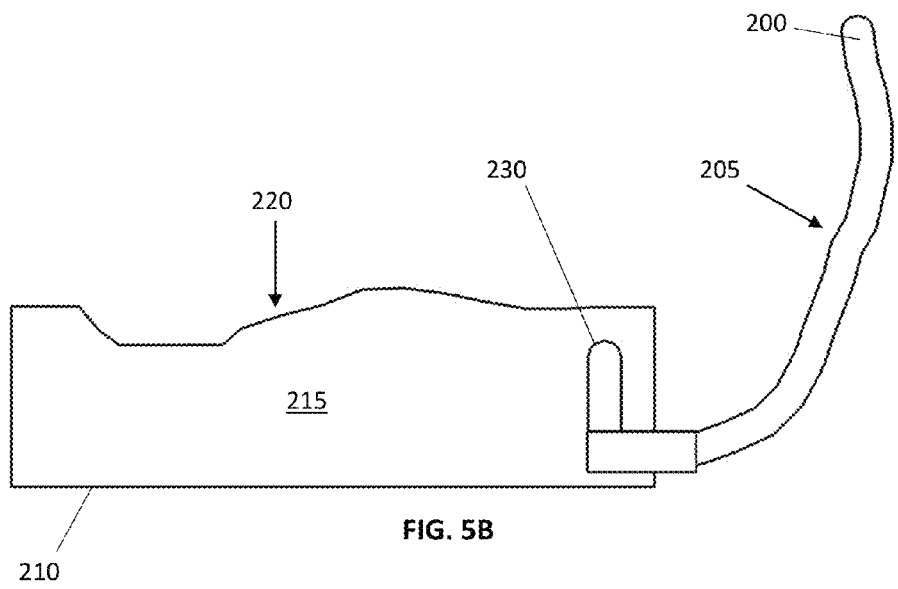
FIG. 5B is a top plan view of the guide and protector of FIG. 5A.

FIGS. 5A and 5B depict an alternative embodiment of a tissue protector 200 and associated cutting guide 210 constructed in accordance with various teaching of the present disclosure. In this embodiment, the tissue protector 200 includes a patient-specific bone facing surface 205 which desirably matches or otherwise conforms to an anatomical structure of the patient's joint, in this case a tibia (not shown). In the exemplary embodiment, the cutting guide 210 includes an upper surface 215 which desirably guides a cutting tool or other instrument, and the cutting guide 210 further includes a patient-specific bone facing surface 220. The tissue protector 200 includes an engagement pin 225 which desirably fits within an engagement slot 230 of the cutting guide 210, with the engagement pin 225 in this embodiment capable of assuming a plurality of positions and/or rotational orientations in the slot 230. In this embodiment, the protector 200 can be selectively attached and/or removed from the cutting guide 210 to facilitate the surgeon's access to the various anatomical structures.

If desired, the bone facing surfaces 205 and 220 of the tissue protector and cutting guide can be designed to match and/or substantially conform to one or more outer surfaces of the patient's bone, with the body of the tissue protector 200 positioned between the bone and a soft tissue surface to be protected (not shown). Desirably, the height H of the tissue protector is designed and/or selected such that the tissue protector will interfere with a surgical cutting tool travelling along the upper surface, such that the tool cannot travel beyond the protector 200 and injure the soft tissues adjacent thereto.

FIGS. 6A through 6D depict another alternative embodiment of a tissue protector 300 and associated cutting guide 310 constructed in accordance with various teaching of the present disclosure. In this embodiment, the tissue protector 300 includes a patient-specific bone facing surface 305 which desirably matches or otherwise conforms to a significant portion of the periphery of an anatomical structure of the patient's joint, in this case a tibia 303 (see FIG. 7). In the exemplary embodiment, the cutting guide 310 includes a first mating surface 315 which mates with an opposing second mating surface 320 of the tissue protector 300, and a guiding surface 312 which can desirably be utilized to guide a cutting tool, as previously described. While in the depicted embodiment the first and second mating surfaces are complex, it should be understood that flat and/or concave/convex surfaces having less complex features could be utilized with varying degrees of utility. In this embodiment, the second mating surface 320 could reference either the patient's bone or the soft tissue protector surface 315 (or both, at various points during a given surgical procedure, if desired) so that the patient specific cutting guide could be used with or without the patient specific soft tissue protector.

In various embodiments, the tissue protector 300 could include a male locking member (not shown) that could slide into a female locking member (not shown) in the cutting guide (or vice versa, with the guide carrying a male locking member, etc.). In such an arrangement, the protector and cutting guide could be secured together into a single unit, such as shown in FIG. 6B. A firm attachment between the tissue protector 300 and cutting guide 310 could desirably ensure that the tissue protector 345 remains in the desired plane 312 of the intended saw cut. In one exemplary embodiment, the male locking member would be in the same plane as the holes 330 and securement pins (not shown) to allow the cutting guide to slide over the securement pins and engage with the female locking member in a single motion.

Figure 6A:
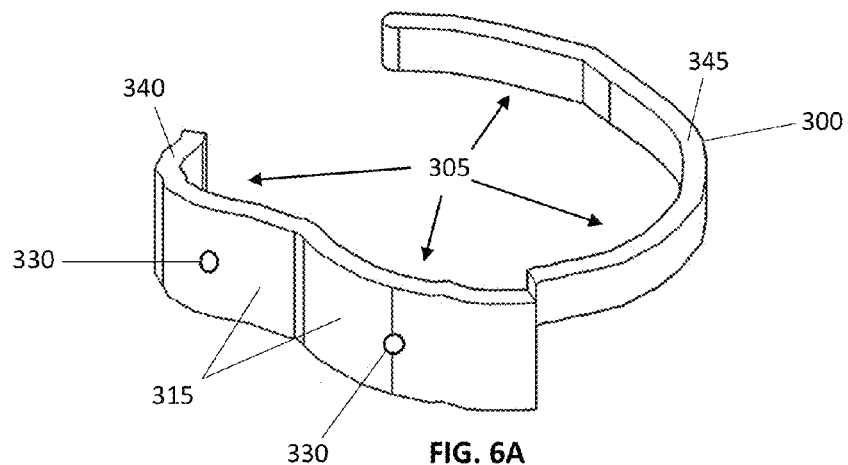
FIG. 6A depicts a perspective view of another exemplary embodiment of a tissue protector.
Figure 6B:
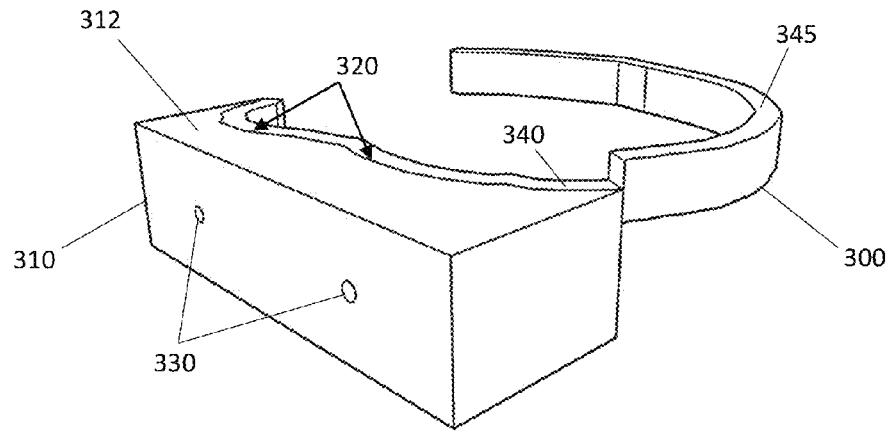
FIG. 6B is a perspective view of the protector of FIG. 6A; with an associated cutting guide.
Figure 6C:
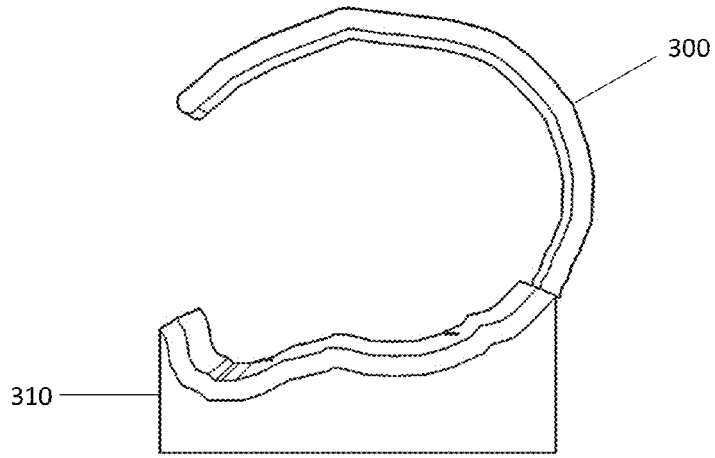
FIG. 6C is a top plan view of the guide and protector of FIG. 6B.
Figure 6D:
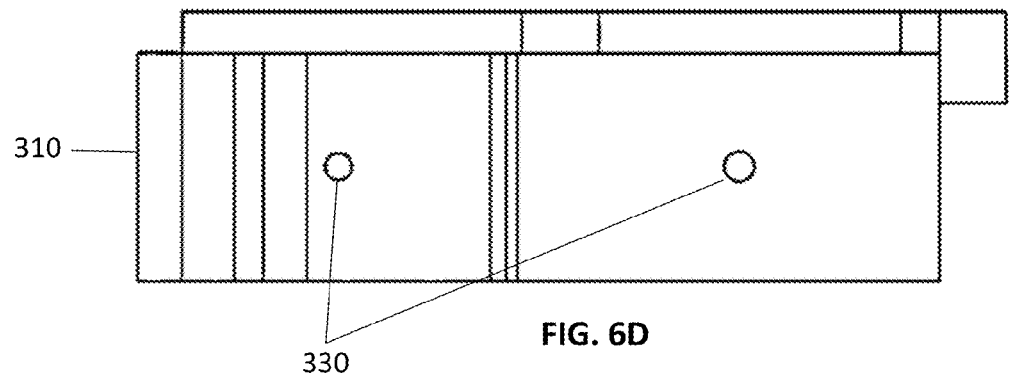
FIG. 6D is a front plan view of the guide and protector of FIG. 6B.

As can best be seen in FIGS. 6A and 6B, the tissue protector 300 and the cutting guide 310 each include pin holes 330, for accommodating securement pins or other features. These pin holes 330 allow one or more securement pins (not shown) to be inserted into and through the cutting guide 310 and the tissue protector 300 and into the tibia, thereby securing the tools to the patient's anatomy. The pins can also desirably secure the cutting guide 310 and tissue protector 300 in a desired alignment, yet allow the cutting guide 310 to be removed (without affecting the positioning of the tissue protector) if desired by the surgeon.

Figure 6E:
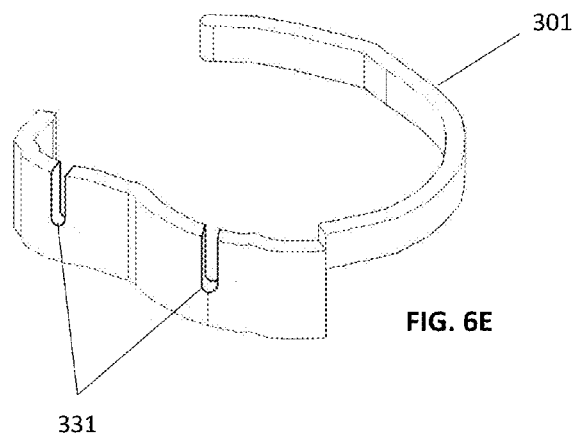
FIG. 6E is a perspective view of an alternative embodiment of the tissue protector of FIG. 6A with a cephalad-extending open slot.
Figure 6F:
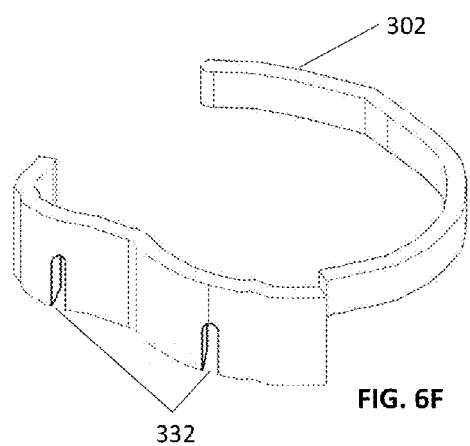
FIG. 6F is a perspective view another alternative embodiment of the tissue protector of FIG. 6A with a caudad-extending open slot.

As best seen in FIG. 6E, the pins holes 331 in the tissue protector 301 could be fully-open slots extending towards a top surface of the protector 301 (i.e., U shaped slots), such that a surgeon could more easily fit the tissue protector over bone and pins at the same time. Alternatively, as best seen in FIG. 6F, the pins holes 332 in the tissue protector 302 could be fully-open slots extending towards a bottom surface of the protector 302. If desired, the cutting guide could include similar open slot arrangements, with the protector including open or closed slots, as desired by the surgeon.

The tissue protector 300 further includes a lower region 340 which will be located proximate to the cutting guide 310, and a raised region 345 located more distally from the cutting guide 310. Desirably, the lower region 340 will not extend above the guiding surface 312 of the cutting guide 310, thereby allowing the surgical cutting tools to pass along the guiding surface 312 and into the targeted anatomy. However, the raised region 345 will desirably extend into the plane formed by the guiding surface 312, desirably interfering with any guided surgical tools and thereby preventing inadvertent damage to adjacent tissue structures.

Figure 6G:
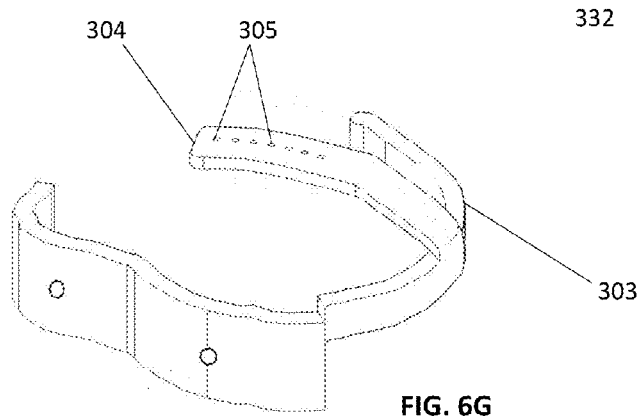
FIG. 6G is a perspective view another alternative embodiment of the tissue protector of FIG. 6A, with a capping arm and protective pin guides.

FIG. 6G depicts a perspective view another alternative embodiment of a tissue protector 303 including a capping arm 304 and protective pin guides 304. In this embodiment, anatomical image data has been used to design an arm 304 which extends over the tibia and desirably includes a series of guide openings 304 through which a surgeon can drill and place 2 or 3 small pins into the tibia, with the pins (when properly positioned) desirably preventing a saw blade from cutting beyond a certain distance into the tibia, thereby preserving an attachment point for the PCL. If desired, this design could allow a surgeon to leave a small piece of bone, which could correspond with a cut out on a tibial tray intended to allow for the preservation of the bone the PCL attaches to.

In the disclosed embodiment, the tissue protector 300 might desirably be formed from a flexible and/or elastic material, such as plastic, to allow the protector 300 to extend around the tibia and "flex" back into place once in a desired position. Alternatively, the protector may be formed of more rigid materials, such as various polymers, metals and/or ceramics, or combinations thereof, as known in the art. Various embodiments of patient specific soft tissue protectors could be made out of nylon, plastic, metal, or other materials.

Figure 7:
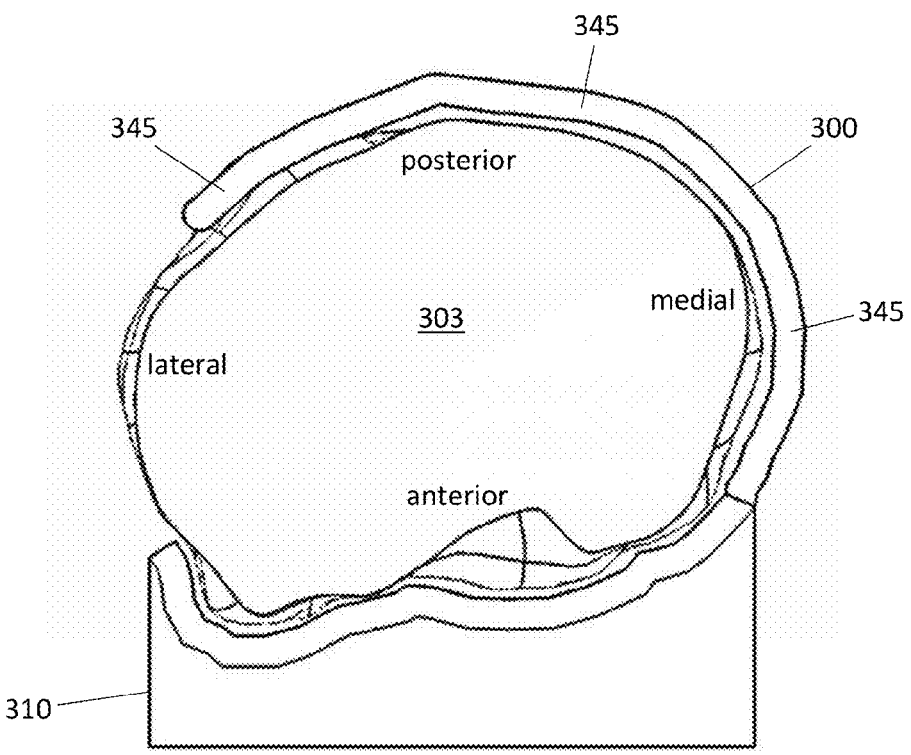
FIG. 7 is a top plan view of the guide and protector of FIG. 6B; positioned adjacent to a tibial bone.

FIG. 7 shows a tissue protector 300 and associated cutting guide 310 in a desired position around a tibia 303. While in this embodiment the protector simply "approximates" the gross anatomy of the tibia, the actual congruence between the patient's anatomy and the protector can more or less match or otherwise conform, depending upon the design of the protector, the accuracy and resolution of the anatomical information of the patient's anatomy, and the designer's objectives and desires. The positioning of the protector 300 in this embodiment has been designed such that the raised region 345 lies adjacent to the posterior and medial regions of the tibia, desirably shielding adjacent soft tissue in those regions, such as the posterior neurovascular structures (i.e., the popliteal artery/vein and the posterior tibial nerve) and the medial collateral ligament (not shown) from inadvertent contact with surgical cutting tools. Because most, if not all, of the posterior structures of the knee joint are not directly visualized during a typical knee joint replacement procedure, the use of such patient-specific tissue protectors can significantly reduce inadvertent damage to soft tissues in protected locations.

Figure 8:
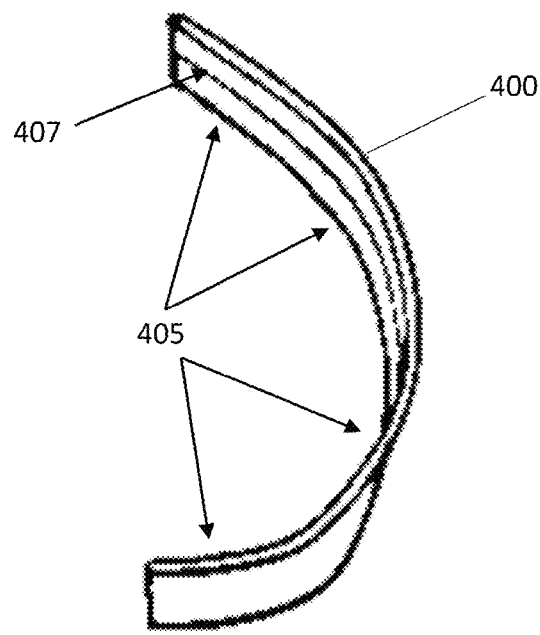
FIG. 8 is a perspective view of another exemplary embodiment of a tissue protector.
Figure 9:
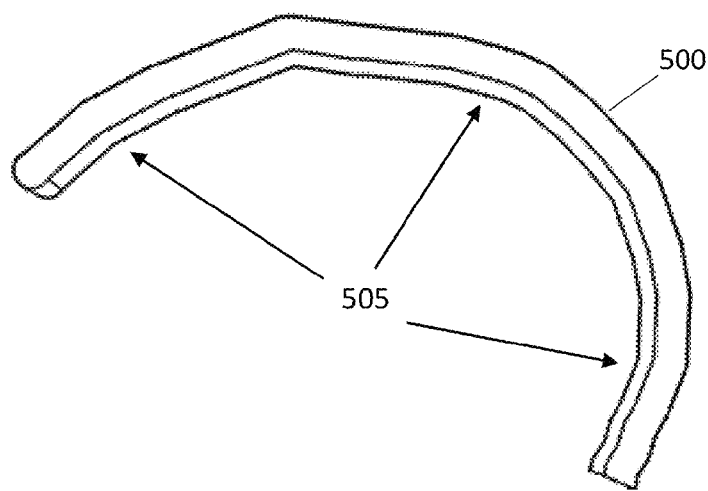
FIG. 9 is a top perspective view of the protector of FIG. 8.

FIGS. 8 and 9 depict additional alternative embodiments of retractors and/or tissue protectors 400 and 500, constructed in accordance with various teaching of the present disclosure. In each of these embodiments, the retractor and/or tissue protector is designed as a one-piece device to be positioned adjacent tissue structures, in a manner similar to a standard retractor. However, the patient-specific features of these embodiments, such as the curvature, shape, size and/or thickness, can be utilized to ensure the retractor is properly positioned to protect the desired anatomy. Desirably, the tissue protector will include at least one patient-specific surface (405 or 505) that substantially matches one or more anatomical features of the patient's anatomy. In use, the surgeon and/or surgical assistant can advance the protector 400 or 500 into the surgical field and slide and/or rotate the protector 400 or 500 along the patient's bone until the matching features of the patient-specific surface 405 or 505 correspond to the underlying anatomy, at which time the protector may inhibit further motion (due to the "interlocking" of the protector and the underlying anatomy). This "interlocking" feature between the protector and the patient's anatomy (which can be possible with the various other embodiments described herein) will desirably confirm proper positioning of the protector, as well as assist in maintaining the protector in a desired position and/or orientation relative to the underlying anatomy (and potentially secure the cutting blocks to the bone so that they do not move during the cutting process).

Accordingly, various patient specific soft tissue protector designs could be used to ensure that cutting blocks are correctly positioned. If the patient specific soft tissue protector did not fit correctly, then the surgeon might need to reconsider the position of the patient specific cutting block.

One additional feature of the tissue protector 400 of FIG. 8 includes a contact or scribed line 407, which indicates where a saw blade of other cutting instrument can be intended to contact the protector 400. In various embodiments, the scribed line 407 may include a step, groove or deep indentation (not shown) that is intended to guide the saw tip (desirably away from sensitive tissues), while in other embodiments, the scribe line may be utilized by the surgeon to determine the positioning of the resection plane and/or cutting instrument (if constructed of or incorporating a material on its face that can be deformed or otherwise marked by the saw blade or other cutting tool). If desired, the protector 400 can be removed from the patient's anatomy and the scribed line 407 examined. If cutting marks (i.e., from the saw blade) are present on the protector adjacent to the scribed line 407, then it could be assumed that the cutting plane is as desired by the surgeon and/or designer. However, if cutting marks are found above and/or below the scribed line 407, this may indicate a misalignment of the cutting tool and/or cut plane, which could negatively affect the performance of the implant components. Such information might prompt the surgeon to recut the anatomy and/or select a different implant component. In this manner, various patient specific soft tissue protector designs could be used to verify the location where the saw blade or other tool might exit a given bone or tissue structure. Such information could be especially helpful to a surgeon to facilitate verification that an anterior femoral bone cut would exit the femoral bone above the anterior cortex of the femur. Such verification could help to prevent anterior femoral notching, a condition that can lead to femoral fracture from weakening of the anterior femoral cortex.

In various embodiments, one or more patient specific soft tissue protectors could be used to facilitate identification of inaccurate bone cuts, which might be caused by deformation of the saw blade in the bone cutting process. When saw blades are used to cut extremely hard bone, they may bend or deform (due to a variety of factors), often resulting in a slightly inaccurate bone cut. However, where patient specific soft tissue protectors such as those described herein are extending around the medial, lateral and/or posterior sides of the bone, the surgeon could identify contact points on the tissue protectors to verify that the tool contact occurred in various proper positions.

Figure 10:
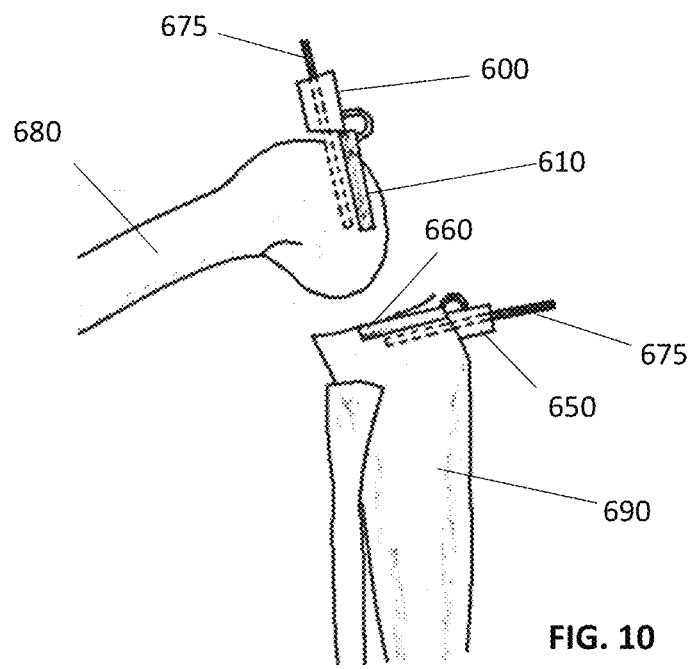
FIG. 10 is a side view of a knee joint, with cutting guides positioned on each of the tibia and femur.

FIG. 10 depicts a side view of a knee joint, showing a femoral cutting guide 600 and associated medial soft tissue protector 610, and a tibial cutting guide 650 and associated medial soft tissue protector 660. Each cutting guide also includes drill or placement pins 675, which extend through pinholes (not shown) in the cutting guides 600 and 610 (as previously described) and extend into the respective femur 680 and tibia 690.

In various embodiments, such as for distal femoral cutting guides (see FIG. 10), patient specific soft tissue protectors could extend off the medial and/or lateral sides of the distal femoral cutting guide and possibly extend around to the posterior side of the cut. If desired, a patient specific distal femoral cutting guide could be attached to an anterior femur in a precise location, with the patient-specific features of the cutting guide desirably matching and/or conforming to anatomical features of the patient's femur. A patient specific medial soft tissue protector could then be attached to the distal femoral cutting guide, such that a thin piece of material with a curvature and/or shape that is specific to the shape of the patient's bone could hug or closely approximate the medial border of the medial femoral condyle, desirably directly in line with where the saw blade would be expected to exit the medial femoral condyle bone. This medial soft tissue protector could extend in a posterior direction from the anterior position of the distal femoral cutting guide and be between the medial femoral condyle and the MCL. Desirably, the medial soft tissue protector would protect the medial collateral ligament in this scenario. If the saw blade accidentally extended beyond the medial femoral condyle bone, then the patient specific medial soft tissue protector could block the saw blade from injuring the MCL. A lateral soft tissue guide could attach in the same way and head in a posterior direction between the lateral femoral condyle and the LCL. The patient specific lateral soft tissue protector could protect the lateral collateral ligament and the patella tendon and bone. The lateral soft tissue protector could continue posteriorly to connect with the medial soft tissue protector. In various embodiments, patient specific soft tissue protectors could also be used to protect the soft tissue structures on an anterior femoral cut (i.e., protect the skin), on a posterior femoral cut (i.e., protect the MCL and LCL), on flange cuts (i.e., protect the MCL and LCL), and on various proximal tibial cuts (i.e., protect the MCL and/or LCL, Patellar tendon and/or posterior neurovascular structures).

Figure 11:
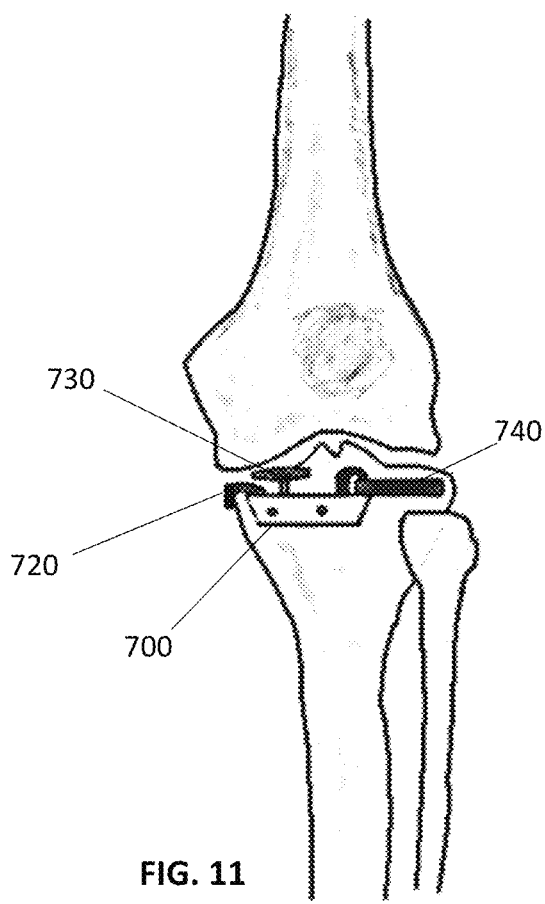
FIG. 11 is a front view of the knee joint of FIG. 10, with a cutting guide positioned on the tibia.

In various alternative embodiments, such as those best suited in conjunction with tibial cuts, a patient specific soft tissue protector could extend off a proximal tibial cutting guide (see FIG. 11). In these embodiments, a surgeon could attach one or more protectors to a patient specific tibial cutting block, including a patient specific medial soft tissue protector that was curved and shaped as a reverse mold of the patient's proximal medial tibial plateau bone, which could hug or closely approximate the medial border of the proximal tibial plateau. In a similar manner, a patient specific posterior tibial protector could attach to the tibial cutting guide and extend over the top of the tibial bone such that a portion of the posterior tibial protector could hug or closely approximate the posterior tibial bone and protect the posterior neurovascular structures from a saw blade exiting the bone if the surgeon pushed the saw blade too far into the proximal tibia. A patient specific lateral soft tissue protector could be positioned between the proximal tibia and the patellar tendon and protect the patellar tendon. FIG. 11 depicts an anterior-posterior view of a knee joint, with a patient-specific proximal tibial cutting guide 700 and various patient specific proximal tibial soft tissue protectors, including a medial tissue protector 720 (for protecting the MCL from a cutting tool), a posterior tissue protector 730 (for protecting the popliteal artery and vein from a cutting tool) and a lateral tissue protector 740 (for protecting the patellar tendon and LCL from a cutting tool).

In various embodiments, the patient specific tissue protectors could attach to a cutting guide after the cutting guide was placed on the bone, or the protectors could be contiguous with and/or attached to the cutting guide and be placed on the bone as one unit. If desired, the patient specific tissue protector could be attached to the bone and then the cutting guide attached to the tissue protector. If desired, a soft tissue protector could be rigidly attached to a patient specific cutting guide, or the protector could be allowed some minor motion and/or rotation so that if the saw blade contacted the soft tissue protector, the soft tissue protector would not vibrate the cutting block excessively and/or change the position of the cutting block.

In various embodiments, such as those described in FIGS. 8 and 9, a patient specific soft tissue protector might not attach to the patient specific cutting blocks at all. Such patient specific soft tissue protectors could reference the articular surface and the sides of the bone and position some material between the intended location of the bone cut and the vital soft tissue structures. Such unattached patient specific soft tissue protectors might be easier to insert as the surgeon would not have them attached to cutting guides. In various embodiments, tissue protectors could comprise a protective cap that could be "clipped onto" an end of portion of a bone before a bone cut was made, with the protector extend vertically along 2 or 3 sides of the bone, and desirably protect surrounding tissues against saw blade excursion in one or more specified directions.

In various embodiments, tissue protectors could be designed to protect against horizontal excursion of the saw blade, vertical excursion of the saw blade, angled excursion of a saw blade, unintended deflection and/or fracture of a saw blade and/or overextension of the saw blade or other cutting tool too far into a bone and/or tissue structure, thereby preventing accidentally injuring soft tissue structures on the other side of the bone.

In various embodiments, a patient specific soft tissue protector could be employed to protect adjacent soft tissue structures as well as provide a surgeon with a visual and/or tactile clue that a saw blade or other surgical tool has exited the targeted bone or anatomical structure. Depending upon the construction and/or constituent material(s) of the protector, contact with the cutting tool might cause the protector to move or vibrate aggressively (or might cause audible indications such as ringing or "pinging" of the saw blade), indicating that saw blade contact has occurred.

In various embodiments, patient specific retractors and/or soft tissue protectors could also be used to improve visibility during a surgical procedure. Currently, standard retractors are employed in a known fashion to "lever off" a bony surface of the patient's anatomy and retract back soft tissue and other bones to improve the surgeon's visibility. These leverage-type retractors will often slip off the bone and move around, primarily because the shape of the retractor does not match the shape of the bone. In contrast, various embodiments described herein could include patient specific soft tissue leverage retractors, which be designed to incorporate one or more surface features that are reverse molds of, or otherwise conform to or match, a specific portion of a bone (if desired, the surface features of the "mold portion" could include various non-patient specific forms designed and/or positioned to engage with the underlying anatomical features, such as hooked or convex/concave shapes). Desirably, a designer will select an anatomical feature of the patient's anatomy that could function as a "pivot point" and/or retain the retractor in a desired position and/or orientation during use (i.e., not slide off the bone or other anatomy when manipulated). Such devices could have a handle or other feature that extends off of the patient specific reverse mold portion to retract back soft tissue and other bones and improve the surgeon's visibility. One exemplary embodiment of a patient specific leverage retractor could be a PCL retractor used to engage the posterior cortex of the tibia and push the tibia forward relative to the femur. This patient specific PCL retractor could be designed to fit the posterior tibial bone and the distal femoral bone and maximize the force used to anterior sublux the tibia relative to the femur. Another exemplary embodiment could include an acetabular retractor that could be placed on an anterior wall of an acetabulum and retract the anterior soft tissue structures for a direct anterior hip approach. Another embodiment could be a hip retractor that could be placed over and/or between the superior or inferior femoral neck, the retractor including one or more patient specific features to engage the underlying patient anatomy and attached to a retractor handle to retract the soft tissue. Another embodiment could be a patient specific glenoid retractor that references the posterior and/or inferior wall(s) of the glenoid, with one or more features to engage with this anatomical structure and used as a pivot point to help pull/push the humerus posteriorly and gain exposure to the glenoid. In the spine, various anatomical features of the vertebral bodies and/or posterior elements could be integrated into a patient-specific retractor and utilized as pivot points to retain the device in a desired anatomical position, such as described herein.

In various embodiments, a retractor could include one or more patient specific or "footprint" features, as well as various patient-specific tissue protector features. Desirably, the retractor could significantly improve visualization of the surgical field while concurrently protecting sensitive tissue structures. Various retractor designs could incorporate patient-specific footprints or other features, similar to those shown in FIGS. 5A, 6A, 8 and 9, with an optional rigid handle (not shown) which can be integrally formed and/or detachably mounted to the footprint.

Figure 12A:
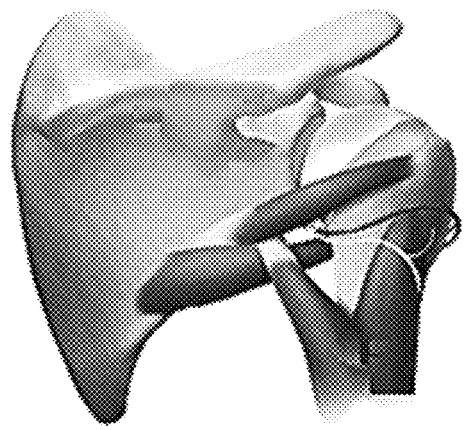
FIG. 12A is a simplified perspective view of a shoulder joint, showing the location and path of a major blood vessel and a major nerve bundle.
Figure 12B:
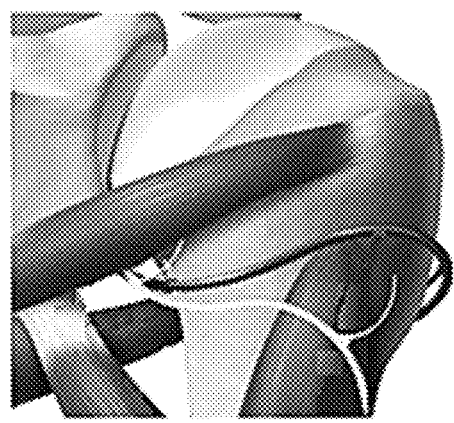
FIG. 12B is a partial expanded view of the shoulder joint of FIG. 12A.
Figure 13:
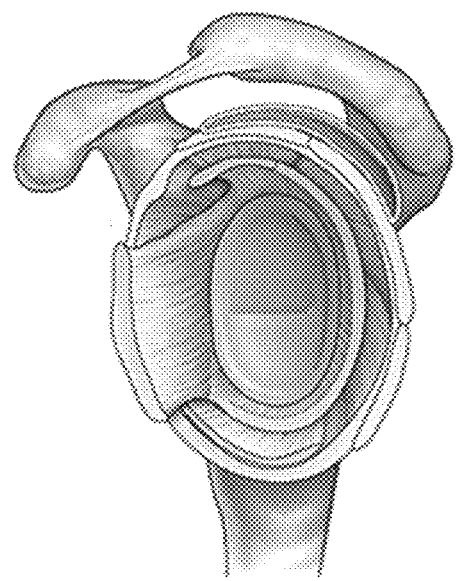
FIG. 13 is a side cross-sectional view of a glenoid socket of a shoulder joint, with associated soft tissues.
Figure 14:
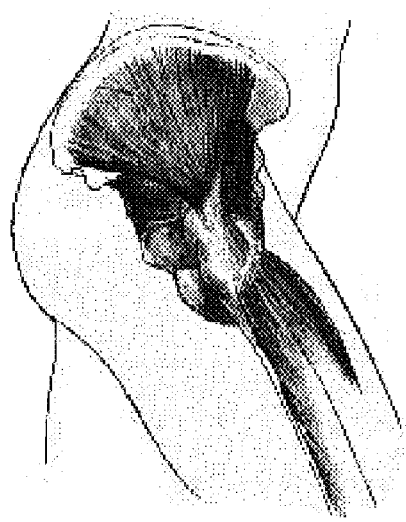
FIG. 14 is a side perspective view of a hip joint and associated soft tissues.
Figure 15:
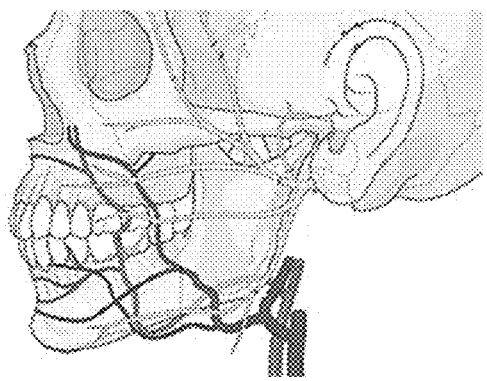
FIG. 15 is a simplified perspective view of a maxillofacial region, showing the location and path of major blood vessels and major nerve bundles.
Figures 16A, 16B:
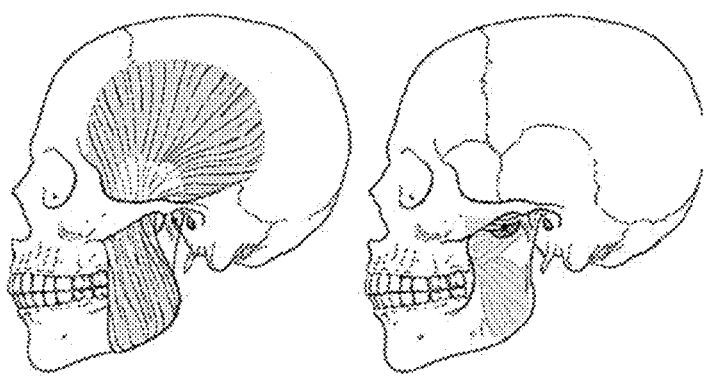
FIG. 16A depicts a skull and maxillofacial region, with associated soft tissue regions.
FIG. 16B depicts the skull and maxillofacial region of FIG. 16A, with additional soft tissue regions depicted.
Figure 17A:
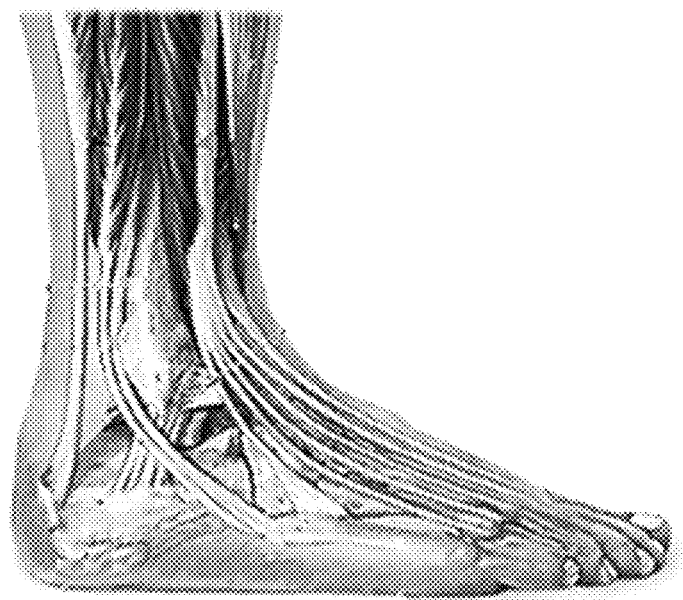
FIG. 17A is a perspective view of lower extremity, showing the location and path of various major blood vessels, major nerve bundles and connective tissues of the foot, ankle and lower leg.
Figure 17B:
FIG. 17B is a cross-sectional view of the lower extremity of FIG. 17A; taken through the ankle.

It should be understood that tissue protectors could be designed for use in any surgical procedure conducted adjacent to a variety of tissue structures in the knee, including medial and lateral collateral ligaments, anterior and posterior cruciate ligaments, patellar tendon, popliteal artery as well as nerve and vein and skin structures. Moreover, various additional embodiments of the patient specific soft tissue protectors and/or other devices described herein could be used in conjunction with various surgical procedures of the knee, as well surgical procedures in other areas of human or animal bodies, including joints such as the shoulder (FIGS. 12A, 12B and 13), the hip (FIG. 14), the skull and maxillofacial area (FIGS. 15, 16A and 16B), the ankle (FIGS. 17A and 17B), the wrist, the spine and neck and/or the elbow.

In a similar manner, tissue protectors could be designed for use in shoulder replacement procedures, as well as during various shoulder surgeries proximate to the rotator cuff tendons (i.e., supraspinatus, infraspinatus, teres minor and subscapularis), bicep tendons and the axillary nerve on the humeral side and the axillary nerve on the glenoid side.

In a similar manner, tissue protectors could be designed for use in hip replacement and/or resurfacing procedures, as well as during various hip surgeries proximate to the anterior and posterior hip capsules, the abductors (i.e., gluteus minimus and gluteus medius) and procedures cutting into the greater trochanter or notching the femoral neck. Such protectors could also be useful during Hip Peri-acetabular osteotomy where multiple bone cuts can be difficult or the sciatic nerve is at risk during the ischial cut.

In a similar manner, tissue protectors could be designed for use in ankle replacement and/or repair procedures, as well as during various ankle surgeries proximate to the EHL, the tibialis anterior and deep peroneal nerve, or where the anterior tibial artery could be cut with a saw blade while making a tibial cut. Similarly, protectors could be useful during surgeries where the Flexor Hallucis Longus or "tibial n" could be damaged when finishing posterior cuts of the ankle.

In a similar manner, tissue protectors could be designed for use in a wide variety of vertebral and/or disk surgeries of the spine, including various spine surgeries involving interbody vertebral fusion with fusion cages, spinal hardware or other structures. If desired, patient specific protectors could be used to protect the nerve roots, the spinal cord, the aorta and/or the vena cava during preparation and insertion of fusion cages, interspinous spaces or other spinal instrumentation from a variety of surgical approaches. Moreover, during ACDF (anterior cervical discectomy and/or fusion), the vertebral arteries and nerve roots could be at risk and might benefit from protectors such as those described herein. In addition, during wedge osteotomy, the spinal nerve roots might benefit from protectors.

In a similar manner, tissue protectors could be designed for use in elbow repair procedures, as well as during various elbow surgeries proximate to the ulnar and median nerve.

In a similar manner, tissue protectors could be designed for use in facial reconstruction and/or repair procedures, as well as during various surgeries involving the mandible or other facial bones, where precise bone cuts may be desired but protection of vital structures like facial nerves is important.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or dearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for protecting a soft tissue structure against injury from a surgical cutting tool during an orthopedic surgical procedure on a patient, comprising;
   obtaining a preoperative scan of a bone of the patient prior to the orthopedic surgical procedure;
   deriving image data from the preoperative scan and using the derived image data to creating a soft tissue protector comprising at least one outer surface contour closely approximating a shape of the patient's bone, the soft tissue protector comprising a flexible material;
   attaching the soft tissue protector to a surgical cutting guide for guiding the surgical cutting tool, the surgical cutting guide including at least one patient-specific contour facing towards the bone, the surgical cutting guide further including at least one cutting surface through which a surgical cutting plane extends, at least a portion of the soft tissue protector spaced apart from the surgical cutting guide and extending into the surgical cutting plane; wherein the surgical cutting tool will contact the soft tissue protector before the surgical cutting tool extends beyond a predetermined angle or distance from the surgical cutting guide.

2. The method of claim 1, wherein the soft tissue protector comprises an elongated body including a patient specific alignment surface that substantially conforms to an anatomical surface of the patient's anatomy.

3. The method of claim 1, wherein the surgical cutting guide comprises a surgical cutting block including at least one alignment feature for aligning a surgical cutting tool along the surgical cutting plane during the orthopedic surgical procedure.

4. The method of claim 2, wherein at least a portion of the elongated body extends outward from the surgical cutting guide and into the surgical cutting plane.

5. The method of claim 3, further comprising cutting at least a portion of the bone along the surgical cutting plane.

6. The method of claim 1, wherein the step of attaching the soft tissue protector to the surgical cutting guide comprises attaching the soft tissue protector to the surgical cutting guide using a detachable attachment feature.

7. The method of claim 1, wherein the step of attaching the soft tissue protector to the surgical cutting guide comprises attaching the soft tissue protector to the surgical cutting guide using a flexible attachment feature that attaches the elongated body to the surgical cutting block so as to allow some minor motion between the elongated body and the surgical cutting block.

8. The method of claim 1, wherein the bone comprises at least one bone from a hip joint of the patient.

9. The method of claim 1, wherein the bone comprises at least one bone from a shoulder joint of the patient.

10. The method of claim 1, wherein the bone comprises at least one bone from an ankle joint of the patient.

11. The method of claim 1, wherein the bone comprises at least one bone from an elbow joint of the patient.

12. The method of claim 2, wherein the anatomical surface of the patient's anatomy comprises a posterior cortex of a tibia of the patient.

13. The method of claim 2, wherein the anatomical surface of the patient's anatomy comprises an anterior wall of an acetabulum of the patient.

14. The method of claim 1, wherein the soft tissue protector further comprises at least one additional surface closely approximating a shape of a portion of a second bone of the patient.

15. A method for protecting a soft tissue structure against injury from a surgical cutting tool during an orthopedic surgical procedure on a patient, comprising;
    obtaining a preoperative scan of a first bone of the patient prior to the orthopedic surgical procedure;
    creating a flexible soft tissue protector comprising at least one protector surface closely approximating a shape of at least a first portion of an outer surface of the first bone, the protector surface being based on the preoperative scan of the first bone;
    providing a surgical cutting guide with at least one cutting guide surface along which a surgical cutting plane extends for guiding the surgical cutting tool, at least a portion of the soft tissue protector spaced apart from the cutting guide surface and extending into the surgical cutting plane; and
    placing the protector surface against the portion of the outer surface of the first bone and utilizing the cutting tool in proximity to the cutting guide surface to cut a second bone surface;
    wherein the surgical cutting tool will contact the soft tissue protector before the surgical cutting tool extends beyond a predetermined angle or distance relative to the cutting guide surface.

16. The method of claim 15, wherein the first bone comprises at least one bone from a hip joint of the patient.

17. The method of claim 15, wherein the first bone comprises at least one bone from a shoulder joint of the patient.

18. The method of claim 15, wherein the first bone comprises at least one bone from an ankle joint of the patient.

19. The method of claim 15, wherein the first bone comprises at least one bone from an elbow joint of the patient.

20. The method of claim 15, wherein the second bone surface comprises a portion of the first bone.

* * * * *